United States Patent [19]

Bartle et al.

[11] Patent Number: 4,603,584
[45] Date of Patent: Aug. 5, 1986

[54] ACOUSTIC DETECTION OF DEFECTS IN STRUCTURES

[75] Inventors: Peter M. Bartle, Suffolk; James C. Needham, Essex, both of England

[73] Assignee: The Welding Institute, Cambridge, England

[21] Appl. No.: 739,764

[22] Filed: May 31, 1985

Related U.S. Application Data

[63] Continuation of Ser. No. 537,654, Sep. 30, 1983, abandoned.

[30] Foreign Application Priority Data

Oct. 6, 1982 [GB] United Kingdom ............... 8228521

[51] Int. Cl.$^4$ ............................................. G01N 29/04
[52] U.S. Cl. ........................................ 73/599; 73/600; 73/602
[58] Field of Search ........................... 73/599, 600, 602

[56] References Cited

U.S. PATENT DOCUMENTS

| | | | |
|---|---|---|---|
| 3,921,126 | 11/1975 | Waters | 367/40 |
| 3,996,791 | 12/1976 | Niklas et al. | 73/602 |
| 4,011,750 | 3/1977 | Robinson | 73/602 |
| 4,128,011 | 12/1978 | Savage | 73/579 |
| 4,342,229 | 8/1982 | Massa | 73/579 |
| 4,400,976 | 8/1983 | Blades | 73/632 |
| 4,400,980 | 8/1983 | Lepert | 73/579 |

OTHER PUBLICATIONS

*Ultrasonics,* Carlin, McGraw-Hill, 1960, pp. 1-2.

*Primary Examiner*—Howard A. Birmiel
*Attorney, Agent, or Firm*—Martin Novack

[57] ABSTRACT

A method of monitoring a structure comprising the steps of:
(a) transmitting a burst of acoustic energy through the structure from a transducer coupled to it,
(b) detecting a received wave resulting from the burst at one or more transducers coupled to the structure, and
(c) monitoring for any change in the structure after a given time (or event) by repeating the steps (a) and (b) with the coupling of the transducers being essentially unaltered, to detect a further received wave or waves; comparing the further received wave or waves with a corresponding reference received wave or waves; and determining for each comparison whether the received wave differs from the reference, any difference being indicative of the formation or growth of a defect in the overall acoustic path travelled by the acoustic energy.

20 Claims, 9 Drawing Figures

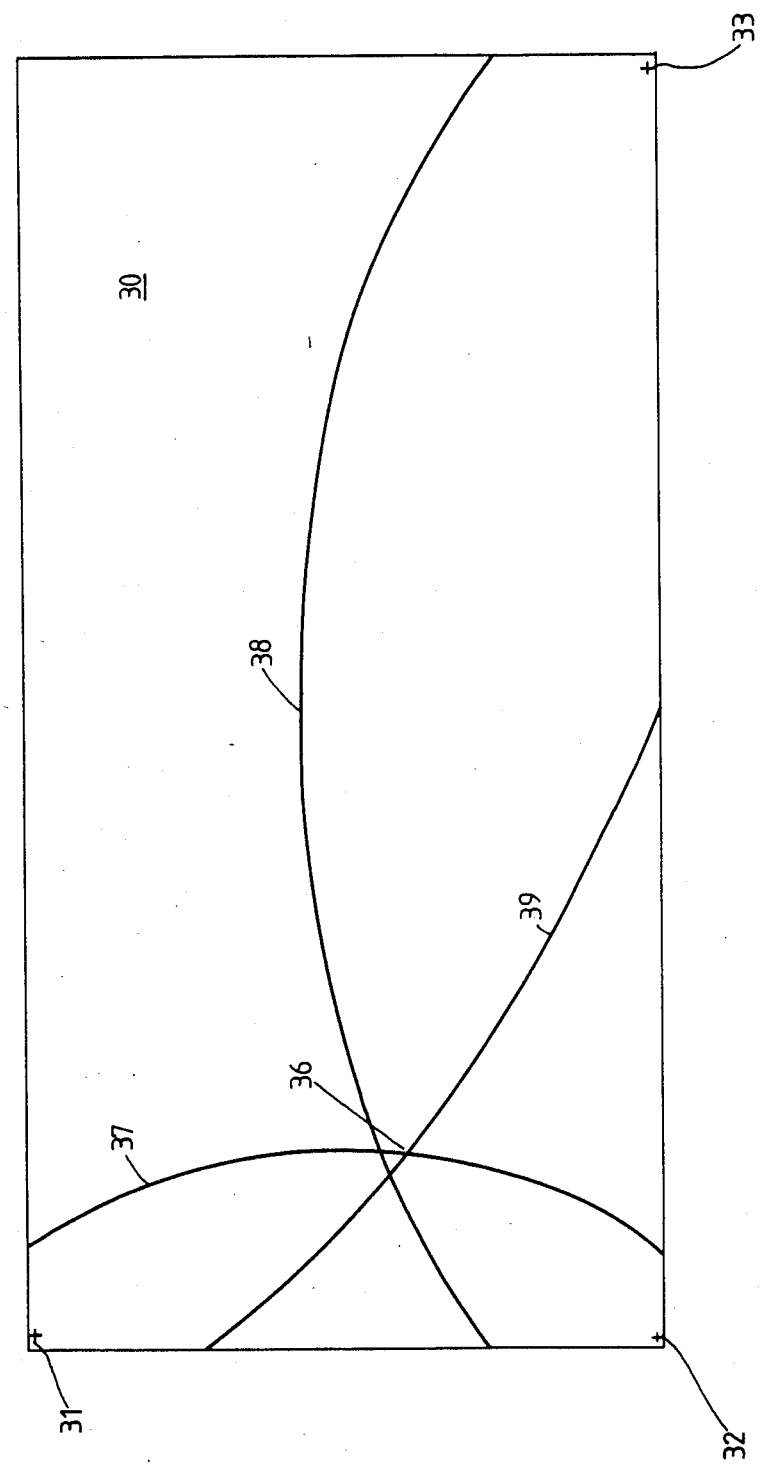

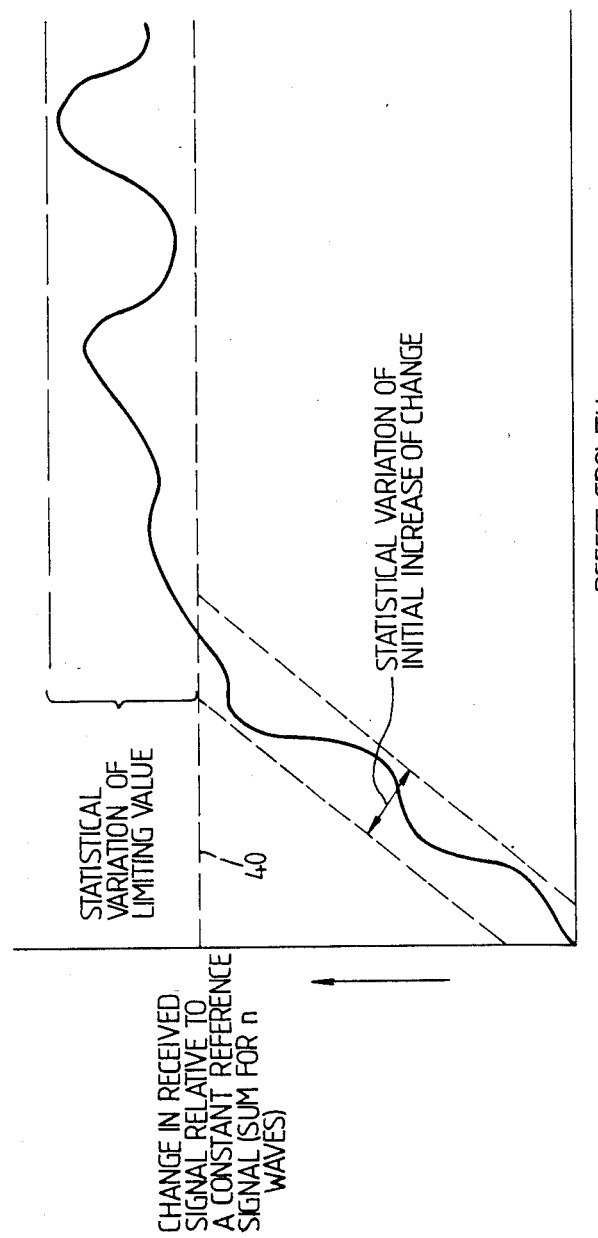

ACOUSTIC DETECTION OF DEFECTS IN STRUCTURES

This is a continuation of U.S. application Ser. No. 537,654 filed Sept. 30, 1983, now abandoned, which claims priority from British Application No. 8228521, filed Oct. 6, 1982.

This invention relates to the monitoring of 'structures' for defect formation and growth, e.g. to locate a defect and to monitor the extent of its growth, by transmitting acoustic pulses through the structure and monitoring them at one or more receiving points.

The term structure is used herein to cover all manner of fabrication in tubular or non-tubular structural metal work and other load bearing construction e.g. oil rig, bridge, pressure vessel, component, or object that may deteriorate in service e.g. may crack under fatigue loading. The term acoustic pulse is used herein to cover an induced elastic wave that for practical purposes would normally have an internal frequency or frequencies in the ultrasonic range e.g. greater than 20 kHz, but could, where acceptable, have an internal frequency or frequencies in the audio range. The term acoustic is used here in a similar wide frequency sense (thousands to millions of Hz). The essential feature of each structure is that it is acoustically continuous e.g. welded or bonded, between the input and receiving points used for monitoring.

Previous techniques used for detecting defects in structures have included acoustic emission analysis, vibration analysis, and ultrasonic flaw detection. Acoustic emission monitoring is a technique based on detecting natural stress waves emitted from defect regions themselves, as a result of deformation, cracking, abrasion etc. Vibration analysis techniques use either service or artificially induced vibration. The vibrations in the structure are analysed with respect to frequency content such that major structural changes are detected, or followed, through changes in the frequency and the amplitude of the resonances caused by the vibration. The generation of these resonances involves vibration of whole elements of the structure.

In ultrasonic flaw detection small areas (e.g. less than 0.2 m wide) of the structure are scanned by short (e.g. 1 to 15 cycles), directional ultrasonic pulses using transducers operating at 1-10 MHz. The transducers are heavily damped and the technique relies on absorbtion or the direct reflection or diffraction of the ultrasonic pulse by a defect in the structure, the leading edge of the returned pulse being detected by the sending or another transducer. The delay between the transmission and receipt of the ultrasonic pulse is dependant upon the position of any defect with respect to the geometry of the structure and the positioning of the ultrasonic transducers involved. The transducers are generally moved across the surface of the structure being examined, in order to provide a scan. Ultrasonic flaw detection is essentially a short range (e.g. less than 1 m in metals) technique requiring considerable movement of the transducers.

These techniques have several disadvantages. Notably acoustic emission detection of stress waves is very difficult for some materials, transducer spacings are usually limited to 2 or 3 m from a suspect source, and data interpretation and source location tend to be problematical. For vibration analaysis the most important information is usually associated with the higher overtones of the structure, which are difficult to stimulate and detect if large structure volumes are to be monitored with any significant degree of sensitivity. Ultrasonic examination is a very short range technique (less than 200 mm) for interrogation of localised areas and requires considerable scanning of the structure, usually with narrow directional beams.

It is an objective of the invention to provide a sensitive technique for the remote detection of the formation or growth of flaws in structures, the technique being sufficiently versatile for use with irregular structures and at ranges of up to 30 m or more. Location of flaws is also within the scope of the invention.

In accordance with the present invention, a method of monitoring a structure comprises the steps of:

(a) transmitting a burst of acoustic energy through the structure from a transducer coupled to it, (b) detecting a received wave resulting from the burst at one or more transducers coupled to the structure, and (c) monitoring for any change in the structure after a given time (or event) by repeating the steps (a) and (b) with the coupling of the transducers being essentially unaltered, to detect a further received wave or waves; comparing the further received wave or waves with a corresponding reference received wave or waves; and determining for each comparison whether the received wave differs from the reference, any difference being indicative of the formation of growth of a defect in the overall acoustic path travelled by the acoustic energy.

In contrast with the already established ultrasonic flaw detection methods, which are concerned only with the sharp leading edge of the received waves generated by a single rapidly damped input to the transmitting transducer, the present technique uses the information available within a significant duration of the received wave. The received wave can be observed, and or recorded (manually or automatically), by any suitable means, including photographic or graphical hard copy, oscilloscope or a VDU display or in a digitised data storer. Similarly, the comparison of the wave forms, and the interpretation can be carried out manually or automatically by any suitable technique. Suitable techniques would include cycle by cycle amplitude comparisons, auto and cross correlation techniques etc. For visual assessment various techniques can be used to highlight differences e.g. displaying the differences between the two waves being compared or displaying each alternately at suitable visual repetition rate.

With this invention it is possible to monitor a structure and to detect, or locate, any defects, particularly growing cracks or broken welds. The defects often form at inaccessable points in the structure. It is particularly relevant to the long term monitoring of complex structures in hostile environments such as off-shore installations, where the technique will enable damage to be detected and give direction for diver inspection whilst also greatly reducing the amount of random diver inspection required. Other areas in which this technique may be used are for monitoring pipe work in refineries and chemical plant, and land pipelines.

In one example of the application of the invention several acoustic transducers are mounted permanently on the surface of a large metal structure such as an off-shore oil platform. From time to time e.g. once a month, an electronic control unit is coupled to all the transducers, and the structure is monitored by comparing acoustic waves received at the various transducers with the corresponding waves stored from previous monitoring sessions. Any difference between each received wave and the corresponding wave received in previous months, which is statistically significant, is indicative of a change in the structure to which the transducers are coupled, providing that the coupling has not altered.

The principle behind the invention is as follows. A first transducer (preferably permanently coupled to the structure) transmits a highly reproducable, usually non-directional, acoustic pulse or burst into the structure. The reproducability of the pulse may be checked by detecting it with an adjacent transducer. This pulse undergoes a complex series of reflections, refractions, diffractions and interferences within the structure and the wave resulting from the original pulse is detected in a receiving transducer. This received wave occurs later in time, and due to multiple reflections etc. is much greater in overall duration than the sending pulse. The receiving transducer is also preferably coupled permanently to the structure; it is generally distinct from the transmitting transducer, but with some geometries it is possible to use the same transducer for both transmitting and receiving. An analysis of the received wave has shown that essentially the time delay between transmission of the pulse and the occurrence of the first change in received wave form for which the defect is responsible, depends on the shortest acoustic path length between the two transducers, on and/or within the structure, and the speed of sound through the medium. We have discovered that in general the pattern of the received wave form, from its start and extending for a considerable period along the wave train does not change for all repetitions over long periods of time, provided that the same pulse is transmitted and that the coupling of the receiving transducers remains effectively unaltered. Moreover, the development, or growth, of any defect in the structure is detectable by the degree of change in the pattern of all or part of the received wave. The received wave is influenced only from, or after the point in time corresponding to the minimum acoustic path length, on and/or within the structure, between the transducers, via the nearest point on the defect.

A further advantage of this technique over conventional ultrasonic techniques is that the power of the applied pulse may lie in the range 0.1 to a few hundred watts depending upon the size of the structure and this enables large areas of the structure to be monitored. For example, intertransducer distances may be up to 30 m or more.

Preferably, step (a) comprises transmitting a series of bursts of acoustic energy having different forms, step (b) comprising detecting the received wave resulting from each burst. For example, each burst of the series of bursts may differ in one or more of its shape, duration, and internal frequency.

The advantage of using a series of bursts of different form is that any one defect may produce a change more readily detected in one received wave form than another.

Preferably, the burst of acoustic energy or each burst of the series of bursts of acoustic energy is repeated between 20 and 200 times, the method further comprising statistically analysing the received waves to minimise the effect of noise.

It is convenient to carry out such a statistical analysis both on setting up the initial reference received wave or waves as well as when detecting the further received wave or waves. Not only will this allow the rejection of excessive values caused by noise but it will permit the normal statistical variation in the waves to be defined and allow more certainty in the detection of the instant at which the first change occurs when attempting to detect the location of the defect, as explained below.

Each transmitted pulse is usually of a constant internal frequency typically lying between 50 kHz and 1 MHz. The technique may be used outside this range, but difficulties are likely to be encountered which will reduce sensitivity and/or neccessitate modifications to the approach. Below about 50 kHz the method has an increasingly poor spacial discrimination and it is difficult to locate the defect or to detect it at all if it is a small defect. Above about 1 MHz the ultrasonic wave is attenuated heavily by the medium, such that the maximum usable intertransducer distances become shorter and shorter. Conveniently, the internal frequency of the pulses lies in the range 150–500 kHz. Preferably, the bursts are repeated at a repetition rate of up to about 200 Hz and conveniently step (a) comprises transmitting bursts at intervals longer than the time for each received wave significantly to attenuate. This is advantageous since this allows the received wave to dampen between bursts preferably to less than 1% of its largest common amplitude. The number of oscillations in each input pulse can be from 1 to 10 for small structures, a few hundred, or even more than one thousand to suit circumstances depending upon the mass and size of the structure and the usable input power.

Since the later cycles of the or each received wave may be excessively sensitive to changes in the acoustic paths, it is preferable to use up to the first 300 cycles of each received wave in the comparison step of step (c).

Preferably, the method further comprises determining for each comparison of the further received wave or waves with the corresponding reference received wave or waves, the point along the received waves at which they first begin to differ; determining the corresponding acoustic path length to the or each transducer via the monitored defect; and determining from at least two such path lengths the location of the monitored defect.

When the occurrence or growth of the defect produces a change in the received wave or waves, and the first change along the wave train can be identified, then the time interval between the start of the transmitted pulse and that first change can be used to calculate the locus of possible defect positions. The approximate defect position can then be calcuated from such loci for the same defect occurence or growth for three suitably positioned pairs of input and receiving transducers.

In some cases, it may not be possible to detect the first change along a received wave and thus the first detected change will not be that produced by the shortest path travelled by the acoustic burst via the defect. In this case, the locus calculated would represent a bound within which lay a defect occurrence or growth. Usually, the fact that the first change had not been detected, would be apparent from a wide "triangle of uncertainty" at the intersection of three loci. It is for this reason that, as mentioned above, it is preferable to use a series of input bursts varying in form so that better location accuracy can be obtained and the chances of detecting the first change along the received wave or waves can be enhanced when the changes are small.

In one convenient method for monitoring the growth or size of a defect, the method comprises monitoring the difference between successive ones of the further received wave or waves and the reference received wave or waves at a point at which they differ. As has been previously mentioned, the size of the difference between the further received wave or waves and the reference wave or waves is indicative of the degree of change of the defect. Essentially, small defect growths will produce small changes in the received wave or waves and larger growths will produce larger changes.

The effect of defect formation or growth gn a given half cycle of the received wave or waves will be to produce a positive, negative, or zero amplitude change. Also, as a growth progresses, a half cycle subject to change will undergo positive, negative, and zero changes in sequence. Thus for any individual cycle the changes, relative to any given starting point will be generally oscillatory, and the starting point could be anywhere in the overall oscillation range. If the absolute changes, i.e. ignoring sign, are summed over a series of half cycles of a received wave then initially the sum will increase as the defect grows; the rate of increase in the sum of the changes will decrease after some defect growth, as the net increase in change for some half cycles in the received wave decreases as a result of a reversal in their direction of change; and a limit will be reached where reversals and increases in change approximately balance. At this limit, it will not be possible to monitor the amount of growth of the defect.

Conveniently therefore the method further comprises determining when the monitored difference approaches or reaches a threshold; and thereupon replacing the reference received wave or waves by the latest received wave or waves to constitute a new reference, and subsequently determining differences between successive ones of the further received wave or waves and the new reference wave or waves.

With this method, the total change in the received waves is not allowed to exceed the threshold mentioned, above which reversals and increases in change will approximately balance. The changes are kept small relatively to the current reference and will thus always increase enabling precise monitoring to be achieved.

In one convenient example, wherein a check transducer is provided adjacent an input transducer, the transducers are mounted in the same housing.

It may be appreciated that this method is particularly suitable for automatic control using a central control unit.

In summary therefore a typical procedure for monitoring defects in a structure, using several permanently mounted transducers is as follows. The transducers are coupled electrically to a central control unit responsible for energising a transmitting transducer and for recording waves from receiving transducers. An electronic memory or mass storage device within the control unit stores the wave forms corresponding to the situation at the time of the original test, which may be months or even years previously. The control unit is programmed to execute a series of transmissions of the input pulse through the structure, and to store and analyse the received wave forms, and to store data on statistical variations in the initial or subsequent received wave forms. The shortest acoustic path lengths to the, or each transducer via any monitored defect are deduced by the control unit, which then uses programmed information concerning the geometry of the structure, and the position of the transducers, to determine the location of the defect. The control unit preferably analyses each received wave in detail, and makes a statistical correlation with previously stored waves. This correlation is then used, first to determine whether a defect has formed or grown, and if so to determine the location of the defect and where possible to determine the extent of its growth.

Some examples of methods in accordance with the invention will now be described with reference to the accompanying drawings, in which:

FIG. 3 illustrates schematically an arrangement for demonstrating the method and additionally illustrates how a defect may be located;

FIG. 5 is a graph illustrating the variation in the change in the received wave form during defect growth; and, FIGS. 6A and 6B illustrate graphically a method of obtaining a continuously increasing change of signal with increasing defect growth.

Figure 1A:
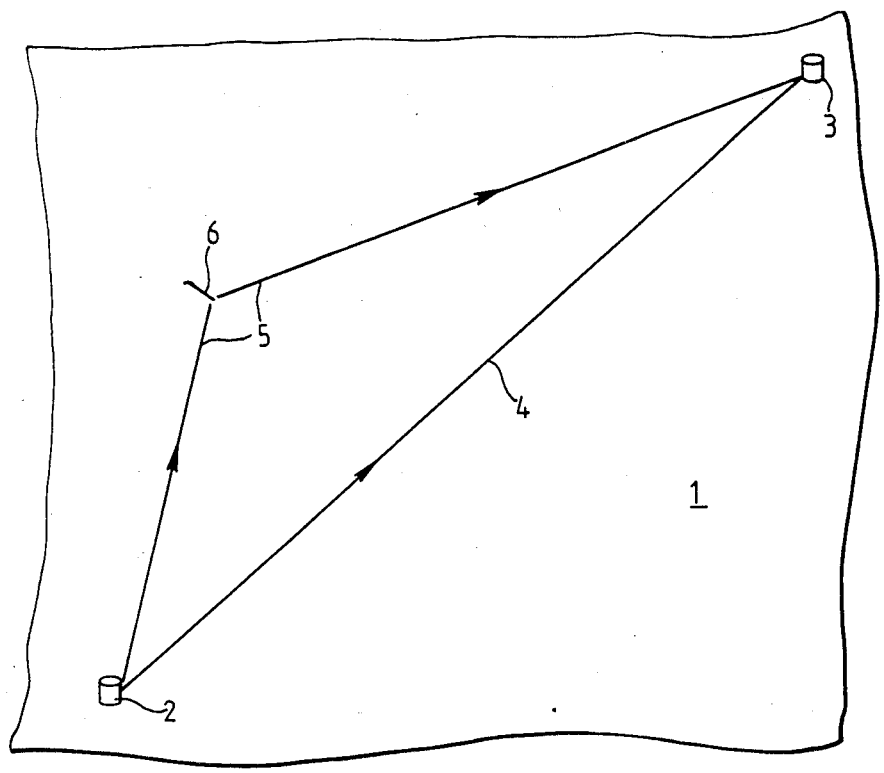
FIGS. 1A and 1B are respectively a schematic diagram of a structure on which are mounted an input transducer and a receiving transducer, and oscillograms illustrating received wave forms before and after the formation of a defect to illustrate the principle of the invention.
Figure 1B:
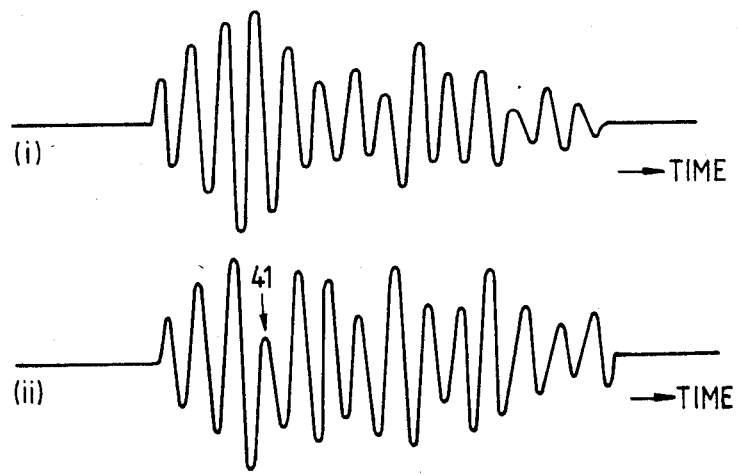

The principle of the invention is illustrated in FIGS. 1A and 1B. FIG. 1A illustrates part of a structure 1 on which are mounted an input transducer 2 and a receiving transducer 3. A short burst, e.g. 5 cycles, of ultrasonic energy is transmitted from the input transducer 2 into the structure 1. The internal frequency of the burst may be for example 400 kHz. After transmission through the structure 1, the burst of energy will be received by the receiving transducer 3 and a wave form similar to that shown in FIG. 1B (i) will result. Due to the fact that the ultrasonic burst will have travelled through many different paths to reach the receiving transducer 3, the number of cycles in the received wave form is greater than that in the input burst. FIG. 1A illustrates just two acoustic paths, the shortest path 4 and a longer path 5.

If a defect, such as a crack 6, forms in the structure 1 and the method is repeated then the wave form received at the receiving transducer 3, as shown in FIG. 1B (ii), will initially be the same as that originally obtained since this will correspond to the shortest path 4 between the transducers 2, 3. However, the presence of a crack 6 in the path 5 will modify the energy passing along the path 5 and this will result in a change in the received wave form once energy transmitted along the path 5 reaches the receiving transducer 3. This change can be seen by comparing the oscillograms in FIG. 1B and is indicated by an arrow 41 in FIG. 1B (ii).

This information can be used simply to indicate that the structure has changed between the two transmissions or the change can be analysed in more detail in order to determine the location of the change and/or the degree of change. This will be explained in more detail below.

Figure 2:
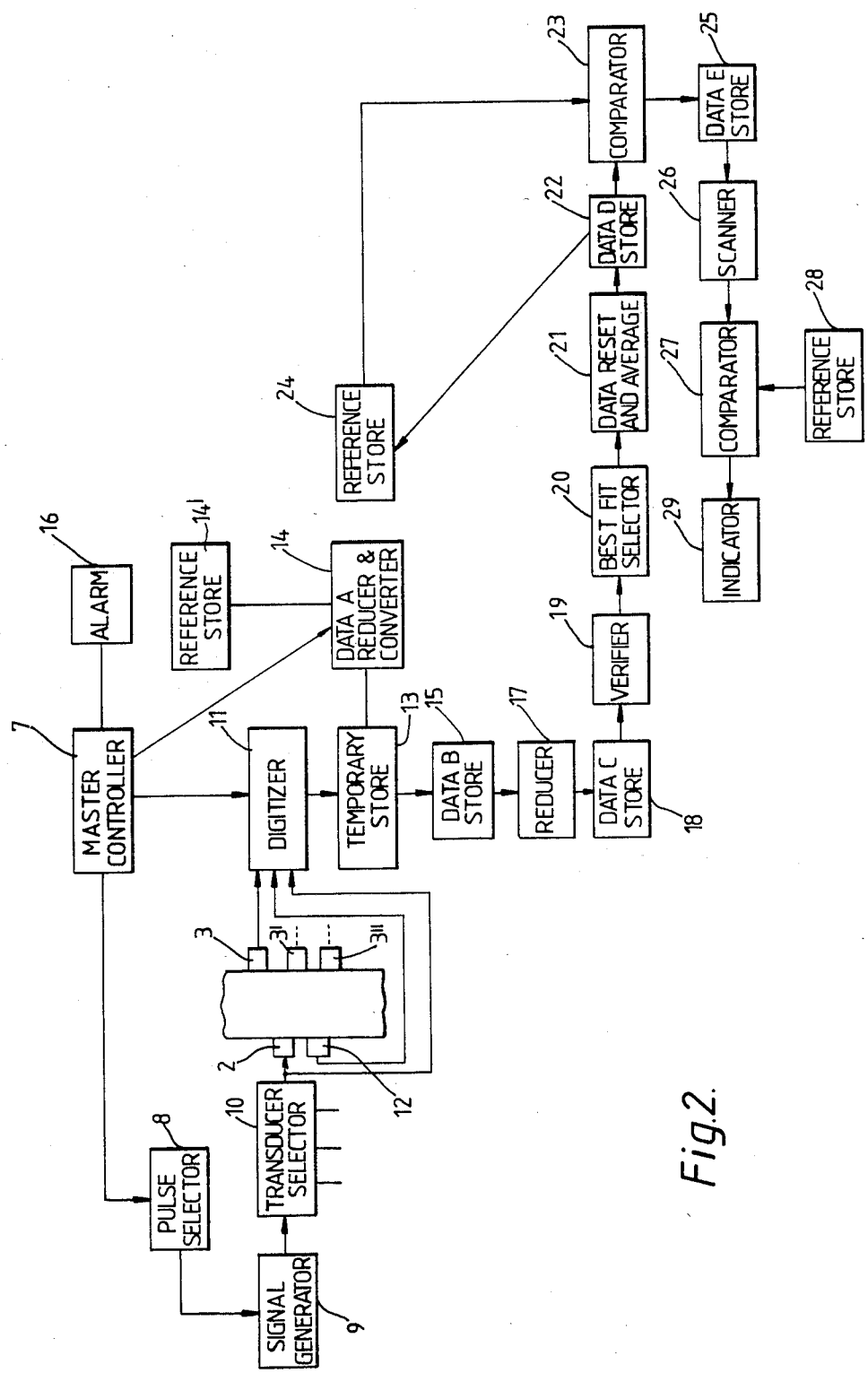
FIG. 2 is a block circuit diagram of apparatus for carrying out an example of the method in accordance with the invention.

An example of apparatus for carrying out the method to provide an output indicating the degree of change in a structure is diagramatically shown by way of a block diagram in FIG. 2. FIG. 2 illustrates part of the structure 1, the input transducer 2 and receiving transducers 3, 3', 3". In practice, there will be more than one input transducer 2 at different positions on the structure 1 or the receiving transducers 3, 3', 3" may be utilised in turn as input transducers with the input transducer becoming a receiving transducer. Operation of the apparatus is controlled by a master controller 7 which may for example be a programmed computer. In practice, the master controller 7 will control operation of most of the data processing units to be described although in FIG. 2, for simplicity, only some connections are illustrated. The master controller 7 controls a pulse selector 8 which selects the form of the pulse to be transmitted. As has been previously mentioned, this may involve selection of internal pulse frequency, number of cycles in the pulse, and pulse shape. The pulse selector 8 causes a signal generator 9 to output a suitable pulse to a transducer selector 10. The transducer selector 10 selects the appropriate input transducer 2 to be energised, only one such connection being shown in FIG. 2. In response to this energisation, the input transducer 2 transmits a pulse through the structure 1 which is received by the receiving transducers 3, 3', 3". Each of these receiving transducers then supplies an appropriate signal to a digitiser 11. In addition, the output from the transducer selector 10 is fed directly to the digitiser 11 while a check transducer 12, mounted adjacent to the input transducer 2, also outputs a signal to the digitiser 11. These latter two signals, after digitisation by the digitiser 11, are temporarily stored as Data A in a store 13. The output from the received transducers 3, 3', 3" are, after digitisation, also fed to the temporary store 13 as Data B. The digital Data A (the input and check signals) are reduced to timings (all timings commencing from the start of the input pulse) of peak amplitudes for each half cycle and timings for each zero crossing in a reducer and converter unit 14. The unit 14 then determines whether each data point in the reduced Data A sequence falls within prescribed limits (set on the basis of reproducability required or practicable as found by experience in relation to the structure being monitored and including a comparison with initial reference Data A stored in a store 14' resulting from an initial transmission) and if the check is satisfactory the Data B is accepted and fed to a store 15. It is important when carrying out the method that the input signal is as identical as possible to an initial reference input signal since it is changes in the received wave forms which may have been obtained many weeks or months apart that are critical. If the master controller 7 determines that the unit 14 has found the Data A unacceptable, an alarm 16 is activated.

The above set of steps is then repeated a preset number "n" of times to obtain "n" sets of Data B. "n" sets of Data B are then obtained for other input signals as determined by the pulse selector 8 and finally all these steps are repeated for each input transducer 2.

It should be understood that although the apparatus is represented by separate blocks in FIG. 2, the data processing to be described can be performed in an appropriately programmed computer.

For maximum sensitivity it is important that small changes in part of a received signal can be readily identified. Consequently, the approach to be described, i.e. comparing small parts of the received signals, is preferred to a single comparison of the signals en bloc.

The data stored in the store 15 is reduced to timings, as previously mentioned in connection with Data A, for each of the "n" received signals by a reducer 17 for the first combination of input signal and input/receiving transducer 2, 3 pair. The new data, called Data C, is stored in a store 18. The "n" data sets within Data C are then compared with each other by a verifier 19 to verify that they are generally the same, allowing for minor digressions, for example where mechanical noise has interfered with a few cycles. "n" typically may lie between 20 and 200.

If the verification is not satisfactory then the alarm 16 will be activated. If, however, the verification is satisfactory then taking the first data set as a reference, the remaining n−1 data sets are, if necessary, time shifted to obtain the best modulation fit with the first data set by a best fit selector 20. The first data points from each of the "n" adjusted data sets are then compared with each other by a data reject and averaging unit 21 so as to reject those not closer to the mean than a preset limit, and to average the rest. This step is then repeated for each data point in the series and results in a new set of data points "Data D" which is taken as defining the wave form recorded for this monitoring occasion and is stored in a store 22.

The above series of steps is then repeated for each Data B set.

Each new set of Data D is then compared by a comparator 23 with a previous set of Data D stored in a reference store 24. The data stored in the reference store 24 may be data from the first monitoring test or a subsequent test where the reference store 24 has been updated. For each data point along the sequence record, the difference between the new data and the reference data is determined by the comparator 23 to derive separate timing and amplitude data, Data E, which is stored by a store 25.

The stored Data E is scanned by a scanner 26 to determine if and where the most recent Data D differs from the reference by more than a "typical" amount. Typical variations for example for half cycles 35 to 40 could be ±1% while the variations could be atypical at 2.5 and above.

The variations determined by the scanner 26 are then compared by comparator 27 with typical and atypical variations previously recorded and stored in a store 28. If the typical or atypical variations are outside the limits previously recorded (or otherwise set) a suitable indication is given by an indicator 29. If the deviations are insufficient to produce this suitable indication then defect growth is deemed not to have been detected (although it may have occurred), and atypical deviations in Data E are noted and stored in the store 28 for later reference.

All the other sets of Data D are then processed in a similar way.

The indication given by the indicator 29 thus tells the operator whether a change has been detected and if a change has been detected this will indicate a new defect or the growth of an old defect.

The Data E can additionally be processed to provide an indication of the location of a defect and/or to provide an indication of the size of the defect or defect growth.

FIG. 3 illustrates the method by which the approximate location of a defect can be determined.

Figure 4A:
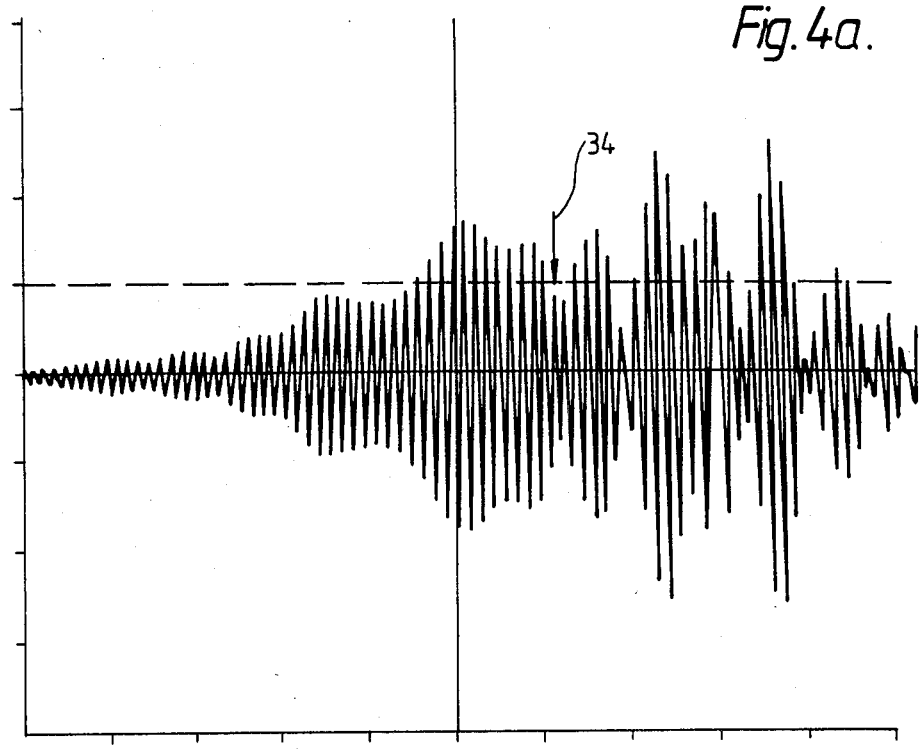
FIGS. 4A and 4B are oscillograms illustrating received wave forms as obtained in the test illustrated in FIG. 3.

FIG. 3 illustrates a steel plate 30 having dimensions 1 m×2 m×6 mm. Transducers 31, 32, 33 are mounted adjacent three of the corners of the steel plate 30. In the test to be described, each transducer 31, 32, 33 was alternately stimulated to generate an ultrasonic burst and the received wave forms at the transducers 33, 33, and 32 respectively were detected. In this test, the initial pulse had an internal frequency of 400 kHz, and comprised 10 cycles. FIG. 4A illustrates the received wave form at the transducer 33 in response to the first transmission from the transducer 31. The oscillogram illustrated in FIG. 4A was then photographically recorded. In a similar way oscillograms corresponding to received wave forms due to pulses generated by transducers 32, 33 were recorded.

Figure 4B:
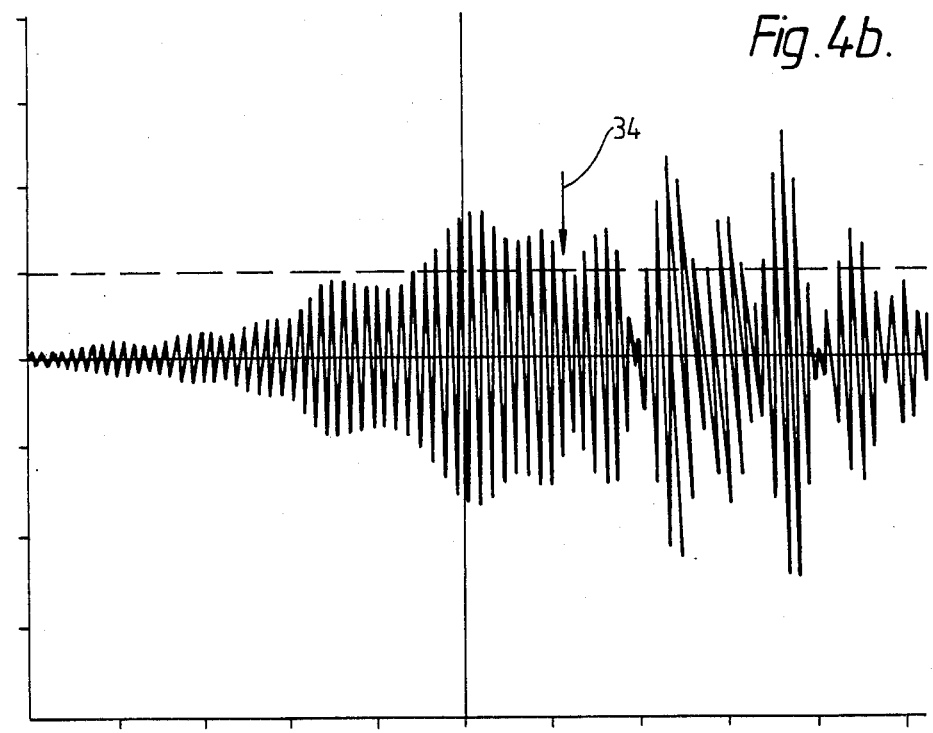

A hole having a depth of 3 mm and a diameter of 2.5 mm was then drilled in the steel plate 30. The same input pulse was then transmitted by the transducer 31 and the received wave form was as illustrated in FIG. 4B. The arrows 34 indicate the occurrence of a first difference between the two received wave forms. This difference is due to the presence of the hole illustrated at 36 in FIG. 3. The time between initiation of the pulse at transducer 31 and the first change between the two received wave forms at the transducer 32 enables an elliptical locus 37 to be drawn around the transducer pair 31, 32 as loci, along which the defect must be positioned.

Input pulses were then generated at the transducers 32, 33 in a similar way to the original setting up input pulses enabling further ellipses 38, 39 to be drawn. In theory, the three ellipses 36, 38, 39 should intersect at the point at which the new defect or growth in defect occurs. In practice, and as is illustrated in FIG. 3, this may not happen if the first change in the wave form cannot be detected with certainty. However, location of the defect or defect growth can be narrowed down to a small area.

It will appreciated that the apparatus illustrated in FIG. 2 can be modified to enable the three or more loci to be determined corresponding to the Data E stored in the store 25.

It is also possible to monitor the growth of a defect. Essentially, an increase in size of any particular Data E represents an increase in size of a defect. However, as mentioned previously, increase in defect size eventually results in a cyclical variation in the difference between the received signal and a reference signal once the difference exceeds a threshold 40. This is illustrated in FIG. 5. Thus, although small changes in defect growth can be quantified, once defect growth exceeds a limit so that the Data E values exceed a threshold, further defect growth cannot be easily determined.

Figure 6A:
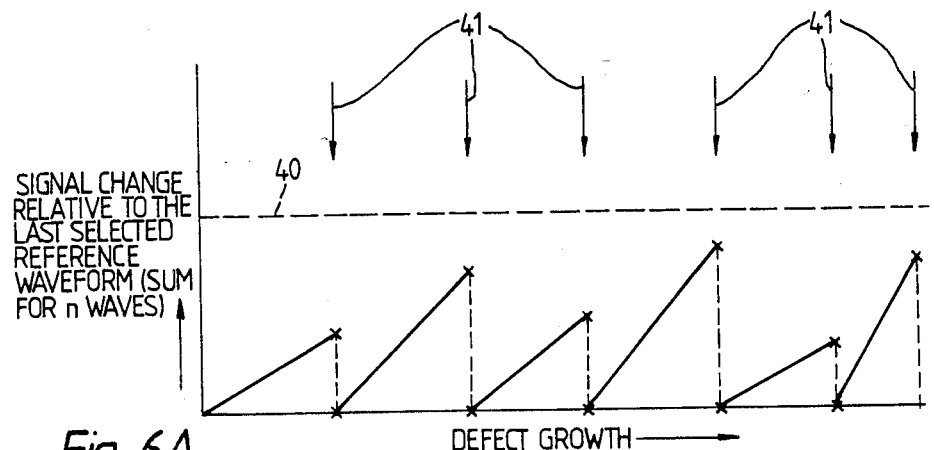
Figure 6B:
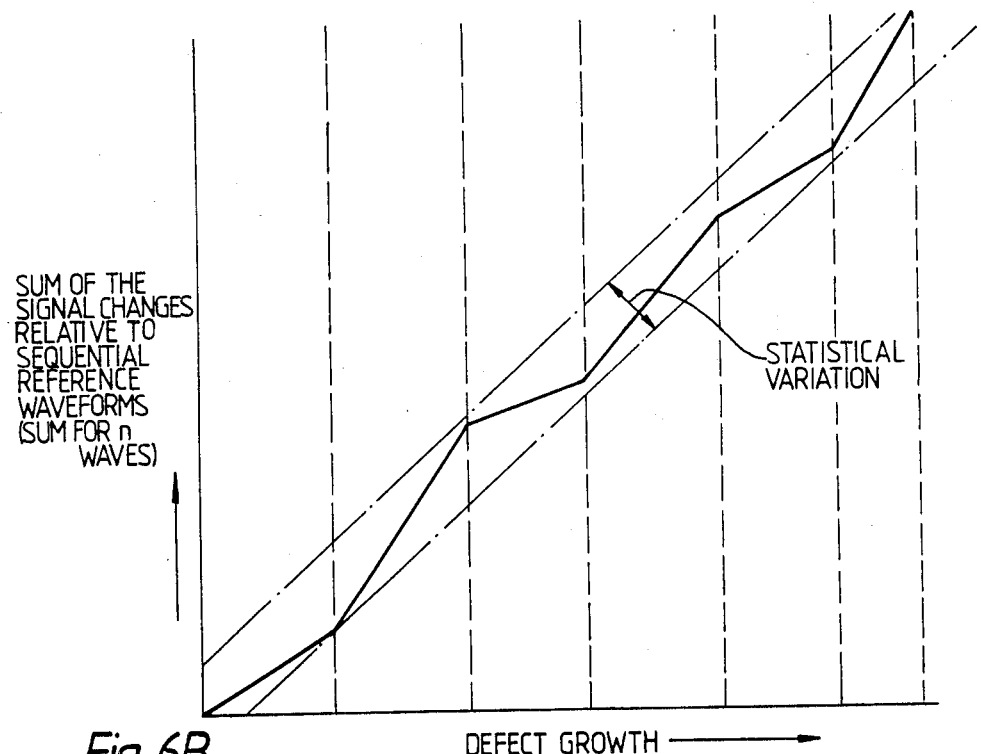

In order to overcome this problem, instead of comparing the Data D values stored in the store 22 with the original Data D values stored in the store 24, the data stored in the store 24 is periodically updated so that differences between new Data D and the reference Data D are maintained below the threshold 40 and these differences are then summed to provide an indication of total change from the original reference Data D. This is illustrated graphically in FIG. 6 where FIG. 6A illustrates variation of the received Data D with respect to the last selected reference Data D. Arrows 41 illustrate the positions at which the reference Data D stored by the reference store 24 is replaced by the latest received Data D. FIG. 6B illustrates how the changes relative to each new reference can be summed and provide a continually increasing overall change representing a continual increase in defect growth. It will be understood that suitable modifications can be made to the apparatus of FIG. 2 to enable defect growth to be monitored.

In view of the importance of utilising substantially identical input wave forms it is preferable if the transducers are permanently mounted to the structure. For example, the transducers may be bonded or glued onto the structure. We have found that it is also possible to accurately replace transducers if they have been removed providing the replacement transducer can be positioned within about 0.1 mm of its original position and orientated within 1 degeree of its original orientation. Conveniently, the transducer comprises a magnetic block with a transducer chip mounted directly on the block.

Resonant PZT crystals in shielded shrouds as used for acoustic emission detection make suitable transmission and receiving transducers. Also amplifiers must have stable gains over the frequency band concerned, for example tuned amplifiers should have the same gain within 1% for frequency shifts of ±10% of the internal frequency of the input burst.

Amplitude digitisers must be at least 8 bit and preferably 10 or 12 bit to maintain accurate discrimination over the range of received amplitudes. Equally for timing, 16 bit accuracy is required to identify zero crossing and instant of peak witin a fraction of one micro-second for total time delays of 1 to 10 milliseconds using for example a 5 MHz clock.

We claim:

1. A method of monitoring a structure to which is coupled at least one input transducer and at least one receiving transducer, the method comprising the steps of:
   (a) transmitting a non-directional burst of acoustic energy into said structure from said at least one input transducer such that portions of said burst travel along a plurality of different paths through said structure, said paths including a shortest path and a plurality of longer paths;
   (b) detecting at said at least one receiving transducer a received wave train resulting from those portions of said burst arriving at said at least one receiving transducer, and
   (c) monitoring for any change in said structure after a given time (or event) by repeating said steps (a) and (b) at least once with said coupling of said transducers being essentially unaltered, to detect at least one further received wave train; comparing corresponding portions of said at least one further received wave train with a previously determined at least one reference received wave train; and determining for each said comparison whether a portion of said received wave train differs from a corresponding portion of said reference received wave train, any difference being indicative of the formation or growth of a defect in the overall acoustic path travelled by said acoustic energy.

2. A method according to claim 1, wherein step (a) comprises transmitting a series of bursts of said acoustic energy having different forms, step (b) comprising detecting the received wave train resulting from each of said bursts.

3. A method according to claim 2, wherein each burst of said series of bursts differs in one or more of its shape, duration, and internal frequency.

4. A method according to claim 1, wherein said burst of acoustic energy is repeated between 20 and 200 times, the method further comprising statistically analyzing said received wave trains to minimize the effect of noise before carrying out step c.

5. A method according to claim 2, wherein each burst of said series of bursts of acoustic energy is repeated between 20 and 200 times, the method further comprising statistically analyzing said received wave trains to minimize the effect of noise before carrying out step c.

6. A method according to claim 1, wherein up to the first 300 cycles of each said received wave train is used in said comparison step of step (c).

7. A method according to claim 1, wherein step (a) comprises transmitting said bursts at intervals longer than the time for each said received wave train significantly to attenuate.

8. A method according to claim 1 for monitoring the growth of a defect, the method comprising monitoring the difference between successive ones of said at least one further received wave train and said at least one reference received wave train at a point at which they differ.

9. A method according to claim 8, further comprising determining when said monitored difference approaches or reaches a threshold; and thereupon replacing said at least one reference received wave train by the latest at least one received wave train to constitute a new reference, and subsequentially determining differences between successive ones of said at least one further received wave train and said at least one new reference received wave train.

10. A method according to claim 1, wherein said internal frequency of said burst of acoustic energy is at least 50 kHz.

11. A method according to claim 1, wherein said at least one further received wave train is compared with said previously determined at least one reference received wave train on a cycle of cycle basis.

12. A method according to claim 1, wherein said burst of acoustic energy has an internal frequency of less than 1 MHz.

13. A method according to claim 1, further comprising determining for each said comparison of said at least one further received wave train with said at least one reference received wave train, the point along said received wave trains at which they first begin to differ; determining the corresponding acoustic path length to the or each said receiving transducer via said monitored defect; and determining from at least two of said path lengths the location of said monitored defect.

14. A method according to claim 2, further comprising determining for each said comparison of said at least one further received wave train with said at least one reference received wave train, the point along said received wave trains at which they first begin to differ; determining the corresponding acoustic path length to the or each said receiving transducer via said monitored defect; and determining from at least two of said path lengths the location of said monitored defect.

15. A method according to claim 3, further comprising determining for each said comparison of said at least one further received wave train with said at least one reference received wave train, the point along said received wave trains at which they first begin to differ; determining the corresponding acoustic path length to the or each said receiving transducer via said monitored defect; and determining from at least two of said path lengths the location of said monitored defect.

16. A method of monitoring a structure to which is coupled at least one input transducer and at least one receiving transducer, the method comprising the steps of:

(a) transmitting a non-directional burst of acoustic energy into said structure from said at least one input transducer, said burst of acoustic energy being repeated between 20 and 200 times;

(b) detecting at said at least one receiving transducer a received wave train resulting from those portions of said burst arriving at said at least one receiving transducer, and statistically analyzing said received wave trains to minimize the effects of noise; and (c) monitoring for any change in said structure after a given time (or event) by repeating said steps (a) and (b) at least once with said coupling of said transducers being essentially unaltered, to detect at least one further received wave train; comparing corresponding portions of said at least one further received wave train with a previously determined at least one reference received wave train; and determining for each said comparison whether a portion of said received wave train differs from a corresponding portion of said reference received wave train, any difference being indicative of the formation or growth of a defect in the overall acoustic path travelled by said acoustic energy.

17. A method according to claim 16, wherein step (a) comprises transmitting a series of bursts of said acoustic energy having different forms, said series of bursts being repeated between 20 and 200 times, step (b) comprising detecting the received wave train resulting from each of said bursts.

18. A method of monitoring the growth of a defect in a structure to which is coupled to at least one input transducer and at least one receiving transducer, the method comprising the steps of:

(a) transmitting a non-directional burst of acoustic energy into said structure from said at least one input transducer;

(b) detecting at said at least one receiving transducer a received wave train resulting from those portions of said burst arriving at said at least one receiving transducer, and (c) monitoring for any change in said structure after a given time (or event) by repeating said steps (a) and (b) at least once with said coupling of said transducers being essentially unaltered, to detect at least one further received wave train; monitoring the difference between successive ones of said at least one further received wave train and said at least one reference received wave train at a point at which they differ; determining when said monitored difference approaches or reaches a threshold; and thereupon replacing said at least one reference received wave train by the latest at least one received wave train to constitute a new reference, and subsequently determining differences between successive ones of said at least one further received wave train and said at least one new reference received wave train.

19. A method of monitoring a structure to which is coupled at least one input transducer and at least one receiving transducer, the method comprising the steps of:

(a) transmitting a non-directional burst of acoustic energy, having an internal frequency of at least 50 kHz, into said structure from said at least one input transducer;

(b) detecting at said at least one receiving transducer a received wave train resulting from those portions of said burst arriving at said at least one receiving transducer, and (c) monitoring for any change in said structure after a given time (or event) by repeating said steps (a) and (b) at least once with said coupling of said transducers being essentially unaltered, to detect at least one further received wave train; comparing corresponding portions of said at least one further received wave train with a previously determined at least one reference received wave train; and determining for each said comparison whether a portion of said received wave train differs from a corresponding portion of said reference received wave train, any difference being indicative of the formation of growth of a defect in the overall acoustic path travelled by said acoustic energy.

20. A method of monitoring a structure to which is coupled at least one input transducer and at least one receiving transducer, the method comprising the steps of:

(a) transmitting a non-directional burst of acoustic energy into said structure from said at least one input transducer;

(b) detecting at said at least one receiving transducer a received wave train resulting from those portions of said burst arriving at said at least one receiving transducer, and (c) monitoring for any change in said structure after a given time (or event) by repeating said steps (a) and (b) at least once with said coupling of said transducers being essentially unaltered, to detect at least one further received wave train; comparing corresponding portions of said at least one further received wave train with a previously determined at least one reference received wave train; and determining for each said comparison of said at least one further received wave with said at least one reference received wave, the point along said received waves at which they first begin to differ; determining the corresponding acoustic path length to the or each said receiving transducer via said monitored defect; and determining from at least two of said path lengths the location of said monitored defect.

* * * * *